United States Patent
Servidio

(10) Patent No.: US 12,329,426 B2
(45) Date of Patent: *Jun. 17, 2025

(54) PRESS FIT STEM

(71) Applicant: Howmedica Osteonics Corp., Mahwah, NJ (US)

(72) Inventor: Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/196,474

(22) Filed: May 12, 2023

(65) Prior Publication Data

US 2023/0277226 A1    Sep. 7, 2023

Related U.S. Application Data

(63) Continuation of application No. 16/749,253, filed on Jan. 22, 2020, now Pat. No. 11,684,398.

(60) Provisional application No. 62/798,000, filed on Jan. 29, 2019.

(51) Int. Cl.

| A61B 17/16 | (2006.01) |
|---|---|
| A61B 17/17 | (2006.01) |
| A61B 17/74 | (2006.01) |
| A61B 17/92 | (2006.01) |
| A61F 2/30 | (2006.01) |
| A61F 2/36 | (2006.01) |
| A61F 2/46 | (2006.01) |
| A61L 27/04 | (2006.01) |
| A61L 27/06 | (2006.01) |
| A61B 17/56 | (2006.01) |

(52) U.S. Cl.
CPC .......... *A61B 17/744* (2013.01); *A61L 27/045* (2013.01); *A61L 27/06* (2013.01); *A61B 17/1668* (2013.01); *A61B 2017/564* (2013.01); *A61B 17/921* (2013.01); *A61F 2/3662* (2013.01); *A61L 2430/02* (2013.01)

(58) Field of Classification Search
None
See application file for complete search history.

(56) References Cited

U.S. PATENT DOCUMENTS

| 4,834,758 A | | 5/1989 | Lane et al. | |
|---|---|---|---|---|
| 5,002,581 A | * | 3/1991 | Paxson | A61B 90/94 |
| | | | | 623/22.44 |
| 5,342,366 A | * | 8/1994 | Whiteside | A61B 90/06 |
| | | | | 606/86 R |
| 5,976,188 A | * | 11/1999 | Dextradeur | A61B 17/8802 |
| | | | | 623/23.23 |
| 6,613,092 B1 | | 9/2003 | Kana et al. | |
| 6,824,566 B2 | | 11/2004 | Kana et al. | |

(Continued)

*Primary Examiner* — Ann Hu
(74) *Attorney, Agent, or Firm* — Lerner David LLP

(57) ABSTRACT

A method of implanting a medical implant includes resecting a long bone along a shaft of the bone so as to form a resected surface and remove a metaphysis of the bone. A tapered bore is reamed through the resected surface of the long bone and into an intramedullary canal thereof. A tapered portion of a stem of a medical implant is fully seated within the tapered bore so as to form a press-fit between the tapered portion of the stem and the long bone and so that a collar disposed at an end of the stem is offset from the resected surface so as to form a gap between the resected surface and the collar.

21 Claims, 12 Drawing Sheets

(56) References Cited

U.S. PATENT DOCUMENTS

| | | | |
|---|---|---|---|
| 6,866,683 B2* | 3/2005 | Gerbec | A61F 2/30734 623/20.15 |
| 7,044,976 B2 | 5/2006 | Meswania | |
| 7,070,622 B1 | 7/2006 | Brown et al. | |
| 7,141,067 B2* | 11/2006 | Jones | A61F 2/28 606/62 |
| 7,435,263 B2 | 10/2008 | Barnett et al. | |
| 7,455,695 B2 | 11/2008 | Khalili et al. | |
| 7,497,874 B1* | 3/2009 | Metzger | A61F 2/38 623/20.15 |
| 7,507,256 B2 | 3/2009 | Heck et al. | |
| 7,799,085 B2 | 9/2010 | Goodfried et al. | |
| 7,867,282 B2 | 1/2011 | Heck et al. | |
| 7,892,290 B2 | 2/2011 | Bergin et al. | |
| 7,909,883 B2 | 3/2011 | Sidebotham | |
| 8,100,982 B2 | 1/2012 | Heck et al. | |
| 8,182,542 B2 | 5/2012 | Ferko | |
| 8,187,336 B2* | 5/2012 | Jamali | A61F 2/30734 623/23.76 |
| 8,535,386 B2 | 9/2013 | Servidio et al. | |
| 8,579,985 B2* | 11/2013 | Podolsky | A61F 2/367 623/22.42 |
| 8,647,388 B2 | 2/2014 | Palmer et al. | |
| 9,101,479 B2 | 8/2015 | Lindsay et al. | |
| 9,149,282 B2* | 10/2015 | Servidio | A61B 17/1717 |
| 9,532,879 B2 | 1/2017 | Lieberman et al. | |
| 9,572,671 B1 | 2/2017 | Palmer et al. | |
| 9,737,408 B2 | 8/2017 | Leszko et al. | |
| 9,814,583 B2* | 11/2017 | Aquilo | A61F 2/3609 |
| 9,943,413 B2 | 4/2018 | Nevins | |
| 10,610,365 B2* | 4/2020 | Librot | A61F 2/30771 |
| 11,109,978 B2* | 9/2021 | Kartholl | A61F 2/3804 |
| 11,684,398 B2* | 6/2023 | Servidio | A61F 2/28 606/62 |
| 2006/0015188 A1* | 1/2006 | Grimes | A61F 2/3601 623/23.22 |
| 2006/0167555 A1* | 7/2006 | Heck | A61F 2/3672 623/20.35 |
| 2006/0167560 A1* | 7/2006 | Heck | A61F 2/384 623/20.15 |
| 2007/0005146 A1* | 1/2007 | Heyligers | A61F 2/367 623/22.41 |
| 2007/0123908 A1* | 5/2007 | Jones | A61B 17/164 606/102 |
| 2008/0281430 A1 | 11/2008 | Kelman et al. | |
| 2010/0114323 A1 | 5/2010 | Deruntz et al. | |
| 2011/0218582 A1* | 9/2011 | Smith | A61F 2/4609 606/86 R |
| 2012/0065638 A1* | 3/2012 | Moore | A61B 17/7225 606/62 |
| 2013/0274889 A1* | 10/2013 | Smith | A61F 2/3672 623/22.46 |
| 2014/0277550 A1 | 9/2014 | Lindsay et al. | |
| 2015/0313611 A1* | 11/2015 | O'Farrill | A61B 17/1617 606/80 |
| 2019/0192304 A1* | 6/2019 | Librot | A61F 2/30771 |

* cited by examiner

PRESS FIT STEM

CROSS-REFERENCE TO RELATED APPLICATIONS

This application is a continuation of U.S. application Ser. No. 16/749,253, filed on Jan. 22, 2020, which claims the benefit of the filing date of U.S. Provisional Patent Application No. 62/798,000, filed Jan. 29, 2019, all of which are hereby incorporated herein by reference.

BACKGROUND OF THE INVENTION

Intramedullary stems are common aspects of implants that replace portions of long bones. Both cylindrical and tapered stems can be utilized to properly fix the implant. When cylindrical stems are used, a separate means of fixating the stem is provided, such as bone cement. Tapered stems form taper locks within the intramedullary canal and do not necessarily require cement for fixation. When portions of the long bone are being replaced, such as in oncology scenarios when a large section of the bone may be removed, a collar can be provided around the stem and against the resected bone surface. The collar can enhance rigidity and stability of the implant, in addition to replacing more of the unoccupied space where the anatomy has been removed.

In prior art devices, implants have used either a tapered stem or a collar, but not both. The reason is because when the tapered stem or the collar becomes fully seated at its adjacent bone surface (i.e. a tapered bore and resected planar surface, respectively), the other would not necessarily be properly and completely seated. This can lead to the implant becoming unstable, particularly if the collar contacts the resected surface before the tapered stem fully locks in place. Moreover, if the tapered stem locks first, a gap can form between the resected surface and the collar, which can leave the open end of the bore in the bone open and prone to infection. Even under the most precise manufacturing conditions, it is nearly impossible to design an implant and prepare a tapered bore in a long bone to such exact specifications that all surfaces are properly seated to lock the implant in place and seal the intramedullary canal of the bone.

Accordingly, there is a need for further improvements in the design of such implants.

BRIEF SUMMARY OF THE INVENTION

A first aspect of the present invention is a method of implanting a medical implant comprising the steps of reaming a tapered bore extending to a first depth in an intramedullary canal of a long bone, the tapered bore having a first diameter at an entry point at the surface of the bone, reaming a counter bore coaxial with the tapered bore extending to a second depth less than the first depth, the counter bore having a second diameter at an entry point at the surface of the bone that is greater than the first diameter, fully seating a distal tapered portion of a stem of a medical implant into the tapered bore so as to form a press-fit between the distal tapered portion of the stem and the long bone, wherein the medical implant further includes a collar disposed around at least a portion of a proximal portion of the stem, the collar having an inner hollow body portion defining an inner surface, and an outer hollow body portion adjustably connected to the inner hollow body portion, and adjusting the collar to advance the outer hollow body portion into the counter bore to a depth less than the second depth.

The step of adjusting includes rotating the outer hollow body portion about the inner hollow body portion so that mating threaded sections of the outer and inner hollow body portions facilitate advancement of the outer hollow body portion into the counter bore. The outer hollow body portion of the collar is prohibited from further movement into the counter bore by the press-fit between the tapered portion of the stem and long bone. The step of fully seating the distal tapered portion of the stem into the tapered bore includes inserting the collar at least partially into the counter bore. The step of fully seating the distal tapered portion of the stem into the tapered bore includes maintaining the collar outside of the counter bore.

According to some examples, at least a portion of the outer hollow body portion remains outside the counter bore. The method may further comprise a step of allowing bone growth between an outer surface of the outer hollow body portion and the bone at the counter bore to seal the reamed bores. In some examples, the outer hollow body portion extension includes a porous portion and the fully seating step includes positioning the porous portion adjacent the long bone within the counter bore so as to promote bone ingrowth into the porous portion. In some examples, the counter bore is cylindrical. The length of the outer hollow body portion extension is less than the second depth.

The method may further comprise a step of attaching another component of the implant to the proximal portion of the stem. The method may further comprise a step of resecting the long bone at a location along a diaphysis of the bone so as to remove a portion of the diaphysis, metaphysis, and epiphysis of the long bone and so as to form a resected end of the long bone. The reaming steps may be performed through the resected end of the long bone.

Another aspect of the present invention is a method of implanting a medical implant comprising the steps of reaming a tapered bore in an intramedullary canal of a long bone, fully seating a distal tapered portion of a stem of a medical implant into the tapered bore so as to form a press-fit between the distal tapered portion of the stem and the long bone, wherein the medical implant further includes a collar disposed around at least a portion of a proximal portion of the stem, the collar having an inner hollow body portion defining an inner surface, and an outer hollow body portion adjustably connected to the inner hollow body portion, and adjusting the collar to advance the outer hollow body portion distally toward a surface of the bone.

The step of adjusting includes rotating the outer hollow body portion about the inner hollow body portion so that mating threaded sections of the outer and inner hollow body portions facilitate advancement of the outer hollow body portion. The outer hollow body portion of the collar may be prohibited from further movement by the press-fit between the tapered portion of the stem and long bone. The method may further comprise a step of allowing bone growth between an outer surface of the outer hollow body portion and the bone to seal the reamed bore. The outer hollow body portion extension may include a porous portion and the fully seating step includes positioning the porous portion adjacent the long bone so as to promote bone ingrowth into the porous portion.

The method may further comprise a step of attaching another component of the implant to the proximal portion of the stem. The method may further comprise a step of resecting the long bone at a location along a diaphysis of the bone so as to remove a portion of the diaphysis, metaphysis, and epiphysis of the long bone and so as to form a resected end of the long bone. The reaming steps may be performed through the resected long bone.

Another aspect of the invention includes another method of implanting a medical implant comprising the steps of reaming a tapered bore extending to a first depth in an intramedullary canal of a long bone, the tapered bore having a first diameter at an entry point at the surface of the bone, reaming a counter bore coaxial with the tapered bore extending to a second depth less than the first depth, the counter bore having a second diameter at an entry point at the surface of the bone that is greater than the first diameter, and inserting a medical implant into the tapered bore and the counter bore, wherein the medical implant includes a stem having a proximal portion and a distal tapered portion, and a collar disposed around at least a portion of the proximal portion of the stem, the collar having a hollow body portion defining an inner surface and an outer surface and a hollow extension extending distally from the hollow body portion, wherein inserting the medical implant includes fully seating the distal tapered portion of the stem into the tapered bore so as to form a press-fit between the distal tapered portion of the stem and the long bone, and moving the hollow extension of the collar into the counter bore to a depth less than the second depth.

The hollow body portion may remain outside the counter bore. The hollow extension of the collar may be prohibited from further movement into the counter bore by the press-fit between the tapered portion of the stem and long bone. In some examples, a largest outer diameter of the collar is greater than the second diameter. According to some examples, a smallest outer diameter of the hollow body portion is greater than the second diameter. In some examples, at least a portion of the hollow extension remains outside the counter bore.

The method may further comprise a step of allowing bone growth between an outer surface of the hollow extension and the bone at the counter bore to seal the reamed bores. The hollow extension may include a porous portion and the inserting step includes positioning the porous portion adjacent the long bone within the counter bore so as to promote bone ingrowth into the porous portion. The hollow body portion may include a distally-facing annular surface connected to the proximal end of the hollow extension, and the distally-facing surface remains separated from the bone surface after implantation of the medical implant. The counter bore may be cylindrical. The length of the hollow extension may be less than the second depth.

The method may further comprise a step of attaching another component of the implant to the proximal portion of the stem. The method may further comprise a step of resecting the long bone at a location along a diaphysis of the bone so as to remove a portion of the diaphysis, metaphysis, and epiphysis of the long bone and so as to form a resected end of the long bone. The reaming steps may be performed through the resected end of the long bone.

Yet another aspect of the invention is a medical implant comprising a stem including a proximal portion and a distal tapered portion, and a collar disposed around at least a portion of the proximal portion of the stem, the collar having a hollow body portion defining an inner surface and an outer surface, and a hollow extension extending distally from the hollow body portion. A largest outer diameter of the hollow extension may be less than a smallest outer diameter of the outer surface of the hollow body portion. The outer diameter of the hollow extension may be substantially constant. The hollow body portion may include a distally-facing annular surface connected to the proximal end of the hollow extension.

A radial thickness of the hollow extension may be substantially constant in a proximal-distal direction. The collar may be a monolithic body, at least a portion of an outer surface of the hollow extension is porous, and the hollow body portion is non-porous. The distal tapered portion may make up a majority of a length of the stem. An outer surface of the proximal end of the stem may be tapered distally, and the inner surface of the hollow body portion is tapered distally for attachment to the outer surface of the proximal end of the stem.

The stem may include a proximal component comprising the proximal portion and a separate distal component comprising the distal tapered portion, a distal end of the proximal component being hollow with an inner surface that is tapered proximally, and a proximal end of the distal component being tapered proximally for attachment to the inner surface of the distal end of the proximal component. The proximal component of the stem has a midsection separating its proximal and distal ends, at least a portion of the midsection having a noncircular outer cross section. The proximal portion of the stem is proximally tapered to accommodate another component of the implant. The distal tapered portion of the stem includes longitudinal ribs spaced circumferentially around an outer surface thereof.

A proximal surface of the hollow body portion of the collar includes two proximally-extending projections. The stem may be made of a non-porous material and the collar is made of a porous material. According to some examples, the stem is made of cobalt chromium and the collar is made of titanium.

Another aspect of the invention is a medical implant comprising a monolithic body including a stem including a proximal portion and a distal tapered portion, and a collar adjacent the proximal portion of the stem, the collar having an extension connected to the stem with a diameter larger than a diameter of the stem, and a body portion connected to the extension with a diameter larger than the diameter of the extension.

Another aspect of the invention includes a method of making a medical implant comprising producing a stem made of a non-porous material including a proximal portion and a distal tapered portion, additively manufacturing a collar made of a porous material having a hollow body portion defining an inner surface and an outer surface, and a hollow extension extending distally from the hollow body portion, and taper locking the collar around at least a portion of the proximal portion of the stem.

Yet another aspect of the invention includes a medical implant comprising a stem including a proximal portion and a distal tapered portion, and a collar disposed around at least a portion of the proximal portion of the stem, the collar having an inner hollow body portion defining an inner surface, and an outer hollow body portion adjustably connected to the inner hollow body portion. An outer diameter of the collar may be substantially constant. At least a portion of an outer surface of the outer hollow body portion may be porous, and another portion of the outer hollow body portion is non-porous. The distal tapered portion may make up a majority of a length of the stem. An outer surface of the proximal end of the stem may be tapered distally, and the inner surface of the inner hollow body portion is tapered distally for attachment to the outer surface of the proximal end of the stem.

The stem may include a proximal component comprising the proximal portion and a separate distal component comprising the distal tapered portion, a distal end of the proximal component being hollow with an inner surface that is tapered proximally, and a proximal end of the distal component being tapered proximally for attachment to the inner surface of the distal end of the proximal component. The proximal component of the stem may include a midsection separating its proximal and distal ends, at least a portion of the midsection having a noncircular outer cross section. The proximal portion of the stem may proximally tapered to accommodate another component of the implant. The distal tapered portion of the stem may include longitudinal ribs spaced circumferentially around an outer surface thereof.

A proximal surface of the inner hollow body portion of the collar may include two proximally-extending projections. When the collar may be seated on the stem, that the two proximally-extending projections are received in two notches in the central portion. The stem may be made of a non-porous material and the collar is made at least partially of a porous material. The stem may be made of cobalt chromium and the collar is made of titanium. An outer surface of the inner hollow body portion and an inner surface of the outer hollow body portion each include threaded sections. A distal end of the outer hollow body portion defines an aperture through which the stem extends, wherein a diameter of the aperture is substantially the same as an outer diameter of the stem adjacent the aperture.

DETAILED DESCRIPTION

FIGS. 1-6 illustrate a press fit stem or implant 10 in accordance with one embodiment of the present invention.

Implant 10 is comprised of a stem 12, a collar 14, and a connector 16. Implant 10 is suitable for use in oncology settings in which a portion of a long bone is removed and replaced with a prosthetic implant. For example, stem 12 can be inserted into the intramedullary canal of a femur, with collar 14 and connector 16 providing a base for a replacement femoral neck and head. This type of replacement requires a robust and secure implant to support and integrate with the new construct.

Figure 2:
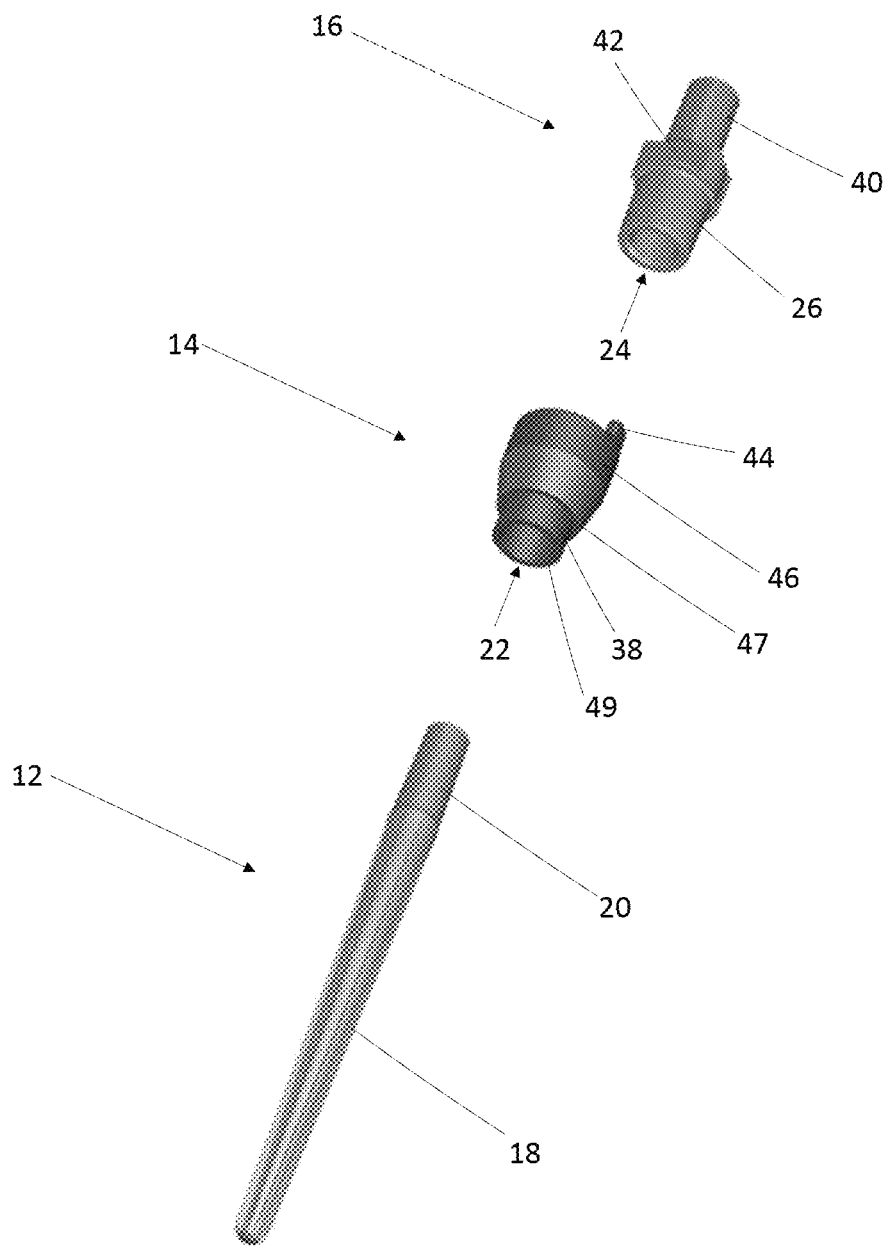
FIG. 2 is a perspective exploded view of the press fit stem shown in FIG. 1.
Figure 3:
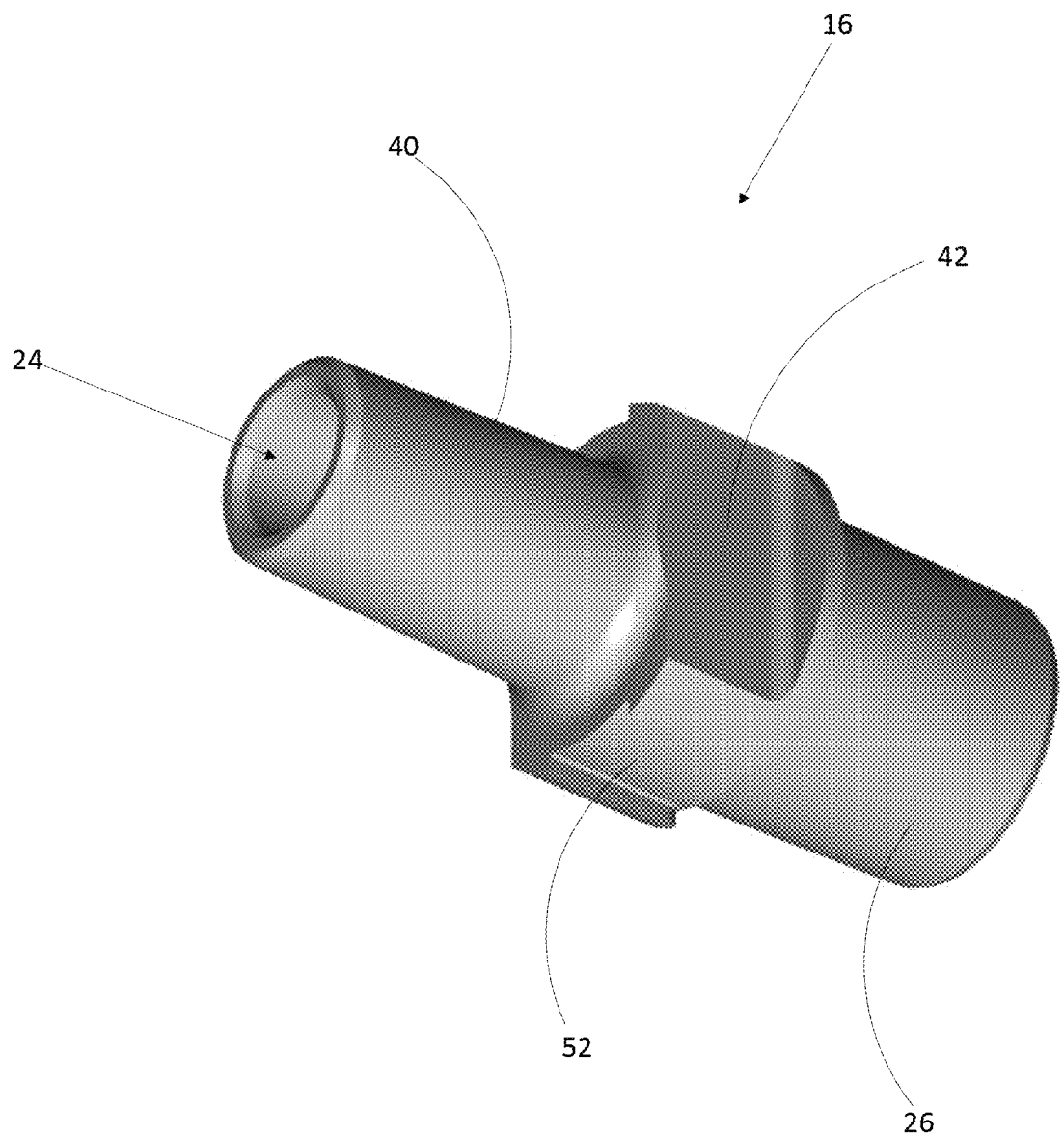
FIG. 3 is a perspective view of a body of the press fit stem shown in FIG. 1.

As shown in FIG. 2, connector 16 is hollow with an extension 26 on its distal end and a mount 40 on its proximal end. The outer diameter of extension 26 is larger than the outer diameter of mount 40. Between extension 26 and mount 40 there is a central portion 42, which has two notches 52 in its outer surface, as best seen in FIG. 3. Tabs or projections 44 extend proximally from the proximal surface of collar 14 and are received in notches 52, respectively. Central portion 42 also has resected portions to give it a noncircular cross section for mating with an engagement tool that can seat and orient connector 16 properly on stem 12. Bore 24 extends throughout the longitudinal axis of connector 16 between its proximal and distal ends, creating the hollowness of connector 16. Distal end of extension 26 fits within the proximal end of a bore 22 of collar 14. Therefore, the outer surface of extension 26 is tapered distally so that it corresponds to the inner surface of bore 22, which is also tapered distally, such that there is a snug tapered connection between extension 26 and bore 22 of collar 14.

In an alternative embodiment, central portion 42 may only have one notch 52 to receive tab 44. In another alternative embodiment, central portion 42 may have three or more notches 52 to receive tabs 44. The number of notches 52 on central portion 42 should match the number of tabs 44 extending proximally from the proximal surface of collar 14.

In another alternative embodiment, the outer diameter of mount 40 may have the same outer diameter as the outer diameter of extension 26. In yet another alternative embodiment, outer diameter of mount 40 may have a larger outer diameter than the outer diameter of extension 26. The tapered mount 40 is prepared for connection to an external implant, such as a femoral neck or head.

Collar 14 is hollow, having bore 22 extending throughout its longitudinal axis between the proximal and distal ends of collar 14. Collar 14 has two main components, a body 46 and an extension 38 extending distally from body 46. In the preferred embodiment, an entirety of bore 22 is tapered distally. In an alternative embodiment, only a distal portion of bore 22 is tapered distally. The proximal portion of bore 22 is sized to receive distal end of connector 16. Other connections besides taper locking are contemplated for connection between collar 14 and connector 16 as long as the connection is secure.

Figure 4:
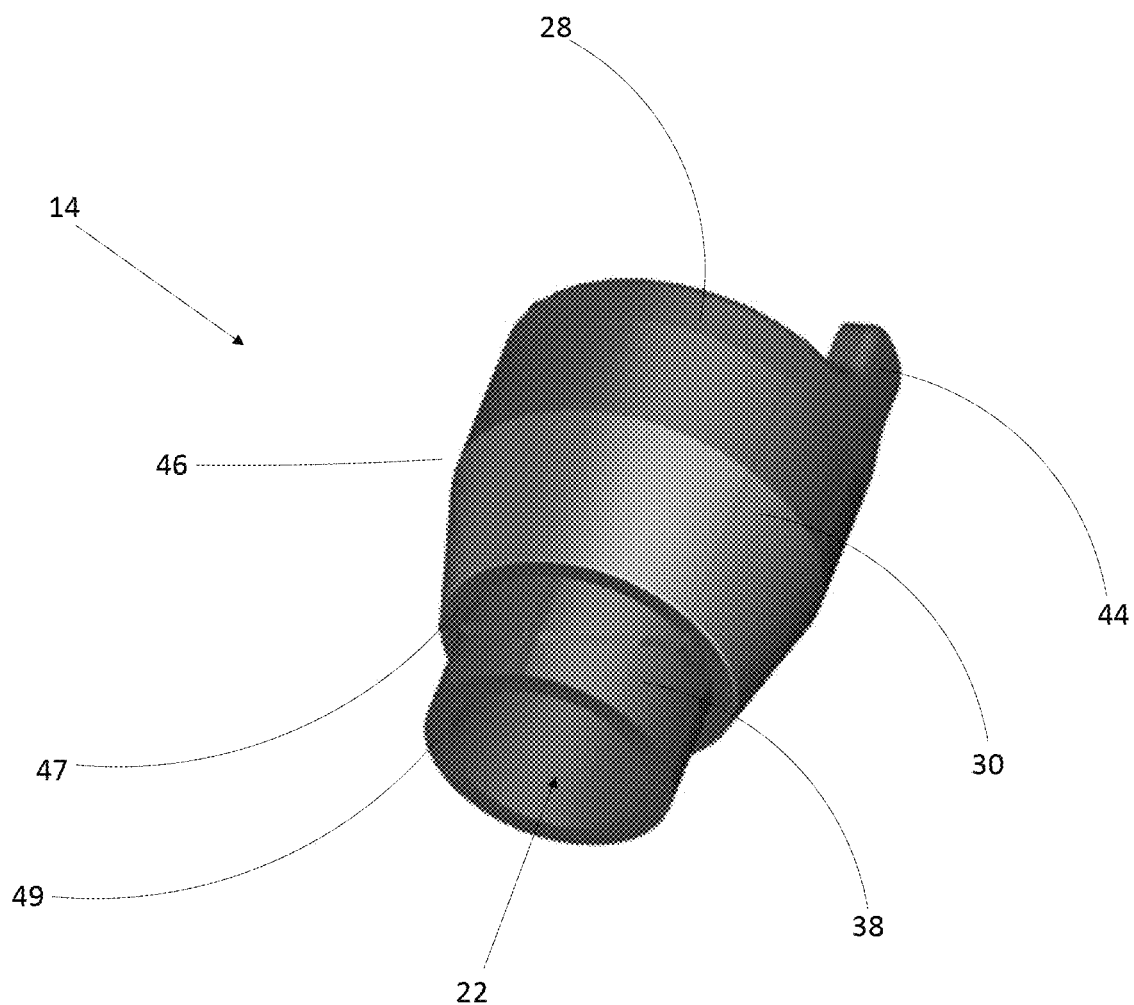
FIG. 4 is a perspective view of a collar of the press fit stem shown in FIG. 1.

As shown in FIG. 4, body 46 has a distally facing annular surface 47 connected to the proximal end of extension 38, which protrudes distally and has a distally facing annular surface 49 at its distal end. Body 46 has a larger outer diameter than the outer diameter of extension 38. The larger outer diameter of body 46 beginning at its proximal end is constant for a certain portion of its length before it tapers to a smaller outer diameter at its distal end, which is still larger than the outer diameter of extension 38. Distally facing annular surface 47 therefore faces distally toward extension 38 and surrounds the proximal end of extension 38. Extension 38 has a substantially constant outer diameter and inner diameter such that its radial thickness measured from a central axis of bore 22 is also substantially constant along different locations of extension 38 in the proximal-distal direction along the central axis. If bore 22 is tapered at extension 38, a varying radial thickness may be provided.

In the preferred embodiment, the outer diameter of the proximal end of collar 14 is a size that allows tabs 44 to be received in the notches 52 of the surface of central portion 42. In an alternative embodiment, the larger outer diameter of the proximal end of collar 14 begins tapering immediately. In another alternative embodiment, the proximal end of collar 14 maintains a constant outer diameter that is larger than the outer diameter of extension 38, such that there is no taper at body 46. The outer diameter of extension 38 is substantially constant. In yet another embodiment, the outer diameter of extension 38 may be changing, such that it has a distal taper. The outer diameter of extension 38 can be any combination of constant or changing so long as it maintains bore 22 and at least a portion substantially conforms with the reamed bone surface of the counter bore in the bone.

Protruding proximally from the proximal surface of collar 14 is at least one tab 44. In the preferred embodiment there are two tabs 44. However, any number of tabs 44 can protrude from the proximal surface of collar 14 to correspond to the number of notches 52 in surface of central portion 42.

Collar 14 is a monolithic body includes both a porous portion 30 and a non-porous, solid portion 28, as best seen in FIG. 4. It is preferred that 1 mm on the outside surface of the collar 14 is porous while the rest is solid. Different portions of the outer surface can be porous, and preferably the distal portion including the entirety of extension 38 that will be adjacent or near bone tissue is made porous to facilitate bone ingrowth. Collar 14 is made of titanium or a similar surgical grade material and can be made by 3D printing or additive manufacturing so that it can include both porous and non-porous portions while remaining a monolithic body. Collar 14 may alternatively be made of other materials or alloys of different materials, such as cobalt chromium (CoCr) or stainless steel (316L). Alternatively, collar 14 can be constructed of different portions or materials and later assembled. As seen in FIG. 7B, porous portion 30 is meant to be positioned adjacent to the long bone 32 within counter bore 34 to promote bone ingrowth into the porous portion 30. The bone ingrowth will cause press fit stem 10 to integrate with long bone 32 for long-term stabilization. Bone ingrowth will also cause press fit stem 10 to become an integral construct leading to a sturdier implant. As such, the patient will experience more success with the implant and less need for future revisions.

In an alternative embodiment, the depth of the porous portion 30 is not limited to 1 mm but rather can be more or less than 1 mm so long as it promotes bone ingrowth into the porous portion. In yet another alternative embodiment, the solid portion 28 does not have to be made of titanium but can be made of any material that is biocompatible for the purpose of an implant.

Collar 14 is a monolithic body, with at least a portion of the outer surface of extension 38 being porous and body 46 being solid. However, in alternative embodiments, there are any number of combinations of the amount of surface of extension 38 and body 46 that is porous and solid. Therefore, the combinations recited in the specification are for exemplary purposes only and are not meant to be limiting. The distal end of collar 14 receives proximal portion 20 of stem 12 within bore 22 such that collar 14 is disposed around at least a portion of the proximal portion 20 of stem 12.

Stem 12 includes proximal portion 20 and tapered distal portion 18. As seen in FIGS. 2 and 5B, proximal portion 20 is tapered proximally for attachment to the inner surface of bore 24 of connector 16, which is also tapered proximally. That is, stem 12 and connector 16 are connectable so that collar 14 can be disposed in its implanted configuration shown in FIG. 6 that is between proximal and distal ends of the bore 24-connector 16 construct. In other words, connector 16 can be considered a proximal component and stem 12 can be considered a distal component of a more traditional stem that has a distal tapered end for seating within the intramedullary canal and a proximal end for connection to another component of the implant, such a femoral neck or head. In an alternative embodiment, proximal portion 20 of stem 12 also at least partially matches a proximal taper within collar 14.

Figure 5A:
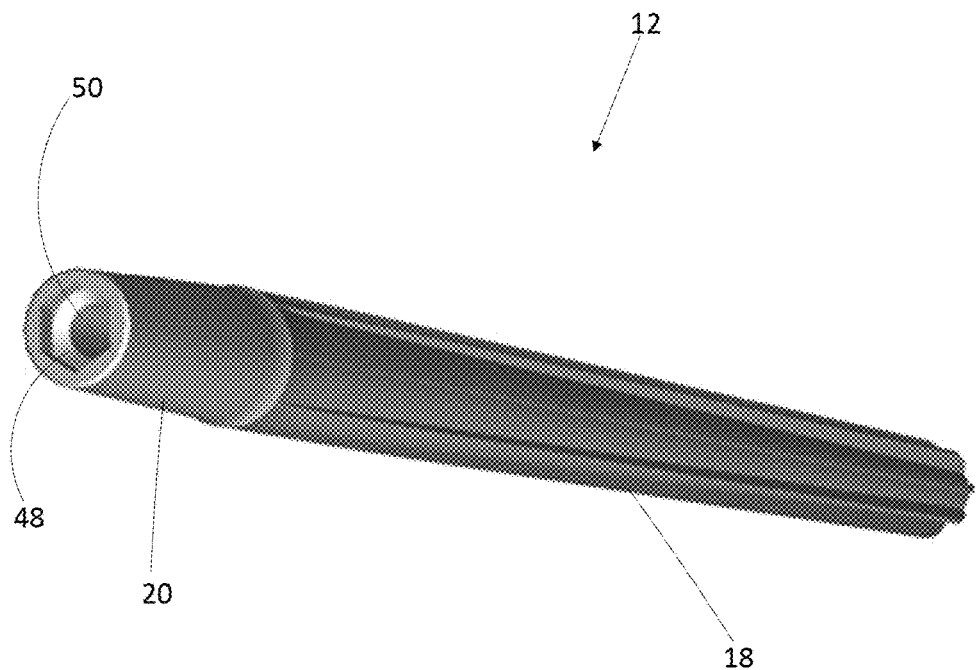
FIG. 5A is a perspective view of a stem of the press fit stem shown in FIG. 1.
Figure 5B:
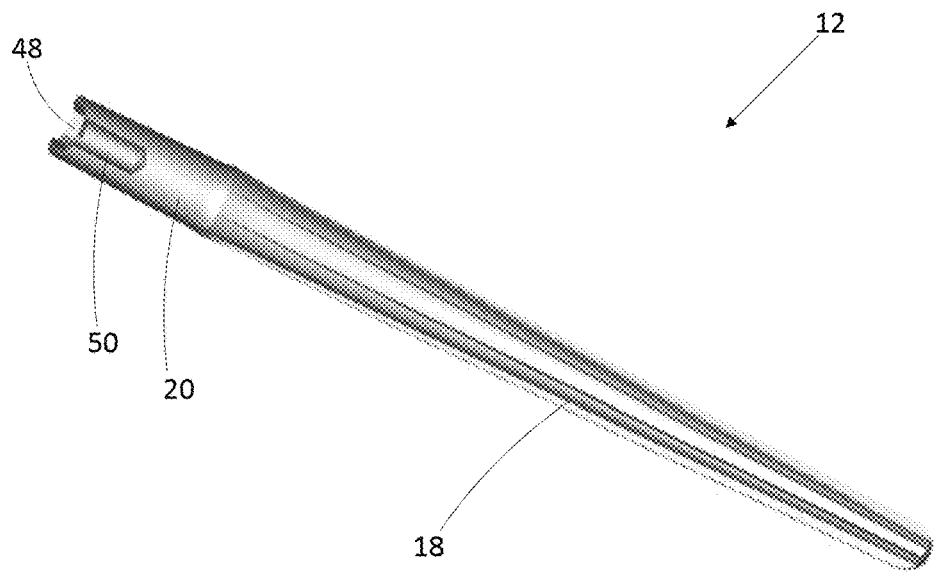
FIG. 5B is a cross-section view of the stem shown in FIG. 5.

As seen in FIG. 5A, the proximal surface of stem 12 includes a hexagonal recess 48 that allows for connection with a tool, such that the tool can maintain its rotational position with stem 12 during insertion. Distal to the hexagonal recess is a threaded bore 50 in which the tool can be connected, as best seen in FIG. 5B. Threaded bore 50 can also accommodate a fixation screw to secure other implants or components to stem 12.

In the preferred embodiment, the tapered portion 18 makes up a majority of the length of stem 12. For example, tapered portion 18 can make up 75%, 80%, 85%, or 90% or more of the length of stem 12. As seen in FIG. 2, tapered portion 18 has a constantly tapered portion with longitudinal ribs spaced circumferentially around an outer surface on the side of stem 12. This provides an antirotation mechanism for press fit stem 10. In the preferred embodiment, the stem 12 is made of a solid, non-porous material. It is preferred that the solid material of the stem 12 is titanium, however, in other embodiments the stem may be made of cobalt chromium or other similar surgical grade materials.

Figure 6:
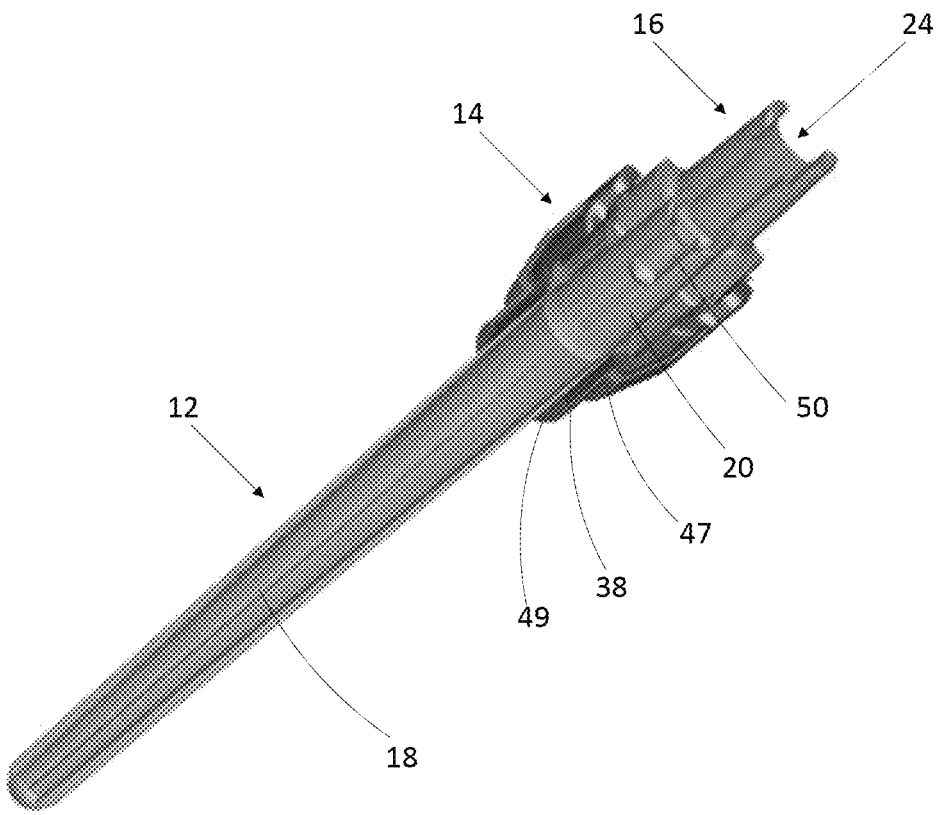
FIG. 6 is a cross-sectional view of the press fit stem shown in FIG. 1.

FIG. 6 is an exemplary embodiment of how stem 12, collar 14, and connector 16 fit together. As shown, stem 12 is within collar 14 and, therefore, also within extension 26 of connector 16. Connector 16 is seated within collar 14.

Figure 7A:
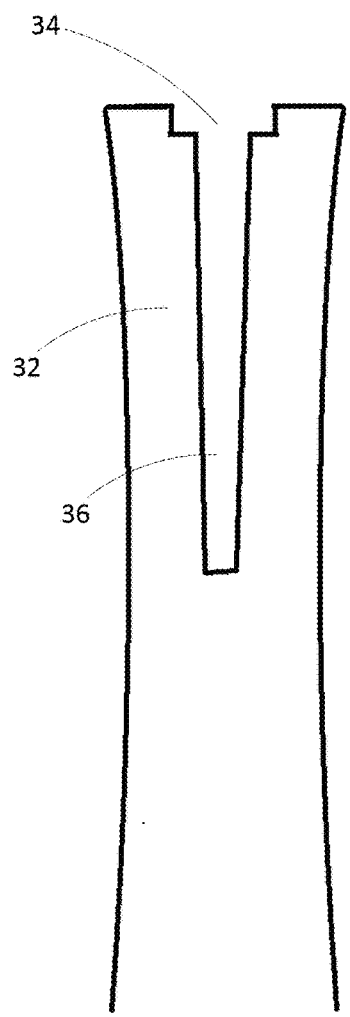
FIG. 7A is a cross-sectional view of a prepared bone.
Figure 7B:
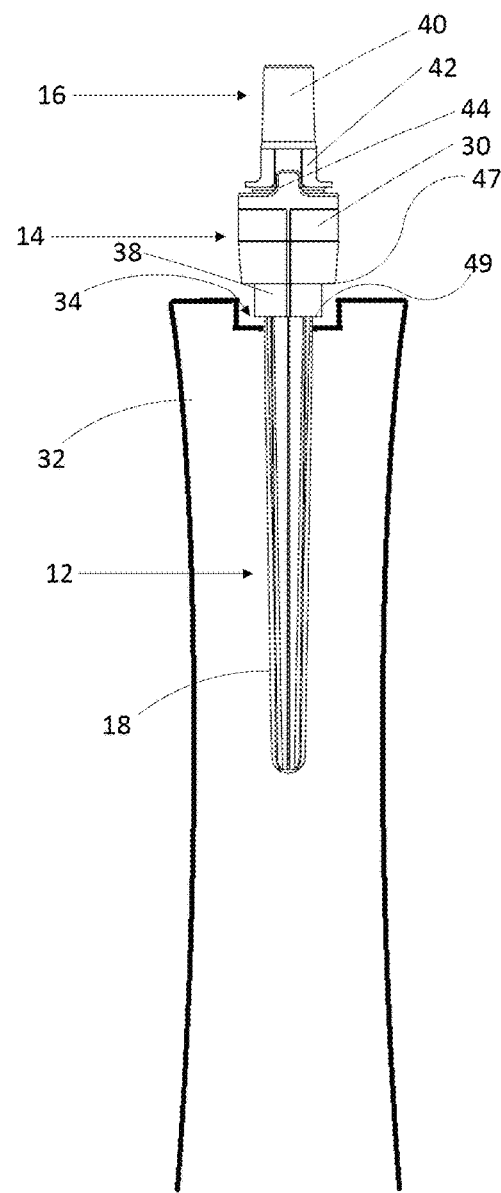
FIG. 7B is a cross-sectional view of the press fit stem shown in FIG. 1 disposed within the prepared bone.

FIGS. 7A and 7B are illustrate how press fit stem 10 is implanted into a long bone 32. As shown in FIG. 7A, a tapered bore 36 is reamed within the intramedullary canal of long bone 32 to a first depth. The tapered bore 36 has a first diameter at the entry point at the surface of the long bone 32.

A counter bore 34 is also reamed into long bone 32 such that counter bore 34 is coaxial with tapered bore 36. The counter bore 34 extends to a second depth that is less than the first depth of the tapered bore 36, as shown in FIG. 7A. The counter bore 34 has a second diameter at its entry point at the surface of the long bone 32 that is larger than the first diameter of tapered bore 36. That is, the preparation of counter bore 34 will widen the section of tapered bore 36 at the bone surface. It is preferred that the counter bore 34 is cylindrical. However, alternative embodiments allow for the counter bore 34 to include a taper or any other non-consistent diameter. This two-stage reaming process can be carried out by separate, appropriately sized reamers for the particular bores. Alternatively, a single reamer can be provided that has a distal tapered portion to match the tapered bore and an enlarged proximal portion to match the cylindrical counter bore. Such a single reamer can be used in a one-stage reaming process where the bone is prepared as shown in FIG. 7A in a single step of using the single reamer.

In the present method, the long bone 32 is first resected before reaming tapered bore 36 and counter bore 34. The resection may occur at a location along a diaphysis of the bone so as to remove a portion of the diaphysis, metaphysis, and epiphysis of the long bone 32. This step creates a planar, proximally-facing surface of the bone from which the bores will be prepared, and the reaming of the counter bore 34 and tapered bore 36 are performed through the resected planar surface of the long bone 32.

Figure 1:
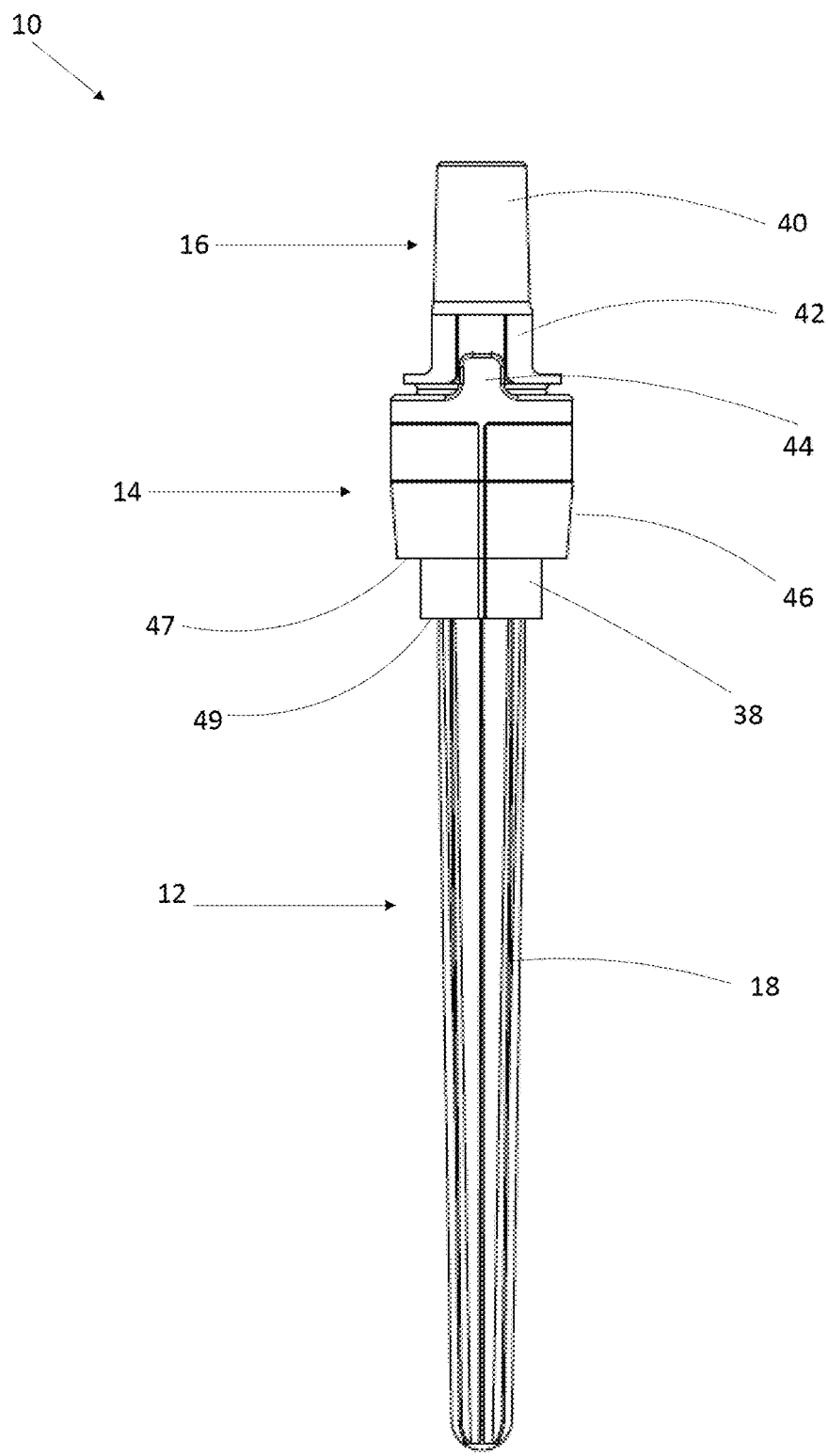
FIG. 1 is a front view of a press fit stem in accordance with one embodiment of the present invention.

Once the long bone 32 is properly reamed to receive stem 12, the distal end of implant 10 is inserted into the tapered bore 36 and counter bore 34 until tapered portion 18 of stem 12 is fully seated within tapered bore 36 to form a press-fit, or taper lock, between the tapered portion 18 of stem 12 and long bone 32. With implant 10 fully assembled as shown in FIG. 1 prior to this step of insertion, this step of inserting stem 12 also includes moving extension 38 of collar 14 into counter bore 34, but not so far as to have distal surface 49 of extension 38 touching the proximally-facing surface at the bottom of counter bore 34. That is, extension 38 is moved into counter bore 34 to a depth that is less than the overall depth of counter bore 34. This step of inserting stem 12 also results in distal surface 47 of body 46 of collar remaining above the resected planar surface of long bone 32 and, thus, outside of counter bore 34. As shown in FIG. 7B, once the implant 10 is properly inserted, neither surface 47 or 49 of collar 38 should be touching a surface of the long bone 32 or counter bore 34. Any contact of surfaces 47 or 49 with the bone could result in a weakening of the taper lock of stem 12 within the tapered bore under loading of press fit stem 10. Any space around extension 38 when extension 38 is within counter bore 34 facilitates bone to grow around extension 38 and into the porous surface 30 of collar 14 to seal the counter bore 34 and tapered bore 36 at the interface between extension 38 and the bone. Therefore, the porous surface 30 of extension 38 is positioned adjacent to or touching the long bone 32 within the counter bore 34 so as to promote bone ingrowth into the porous portion.

Further movement of extension 38 into counter bore 34 is prohibited by the press-fit between the tapered portion 18 of stem 12 and long bone 32. As there is a press-fit, tapered portion 18 of stem 12 will not be able to move further distally within tapered bore 36 thus preventing any distal movement of other components of press fit stem 10.

In this implanted configuration of implant 10, body 46 of collar 14 remains outside the counter bore 34. At least some of extension 38 may also remain outside of counter bore 34, such that the distally facing annular surface 47 of body 46 remains separated from the bone surface after implantation of implant 10. However, the portion of extension 38 that is located within counter bore 34 allows bone growth so that implant 10 achieves its purpose of sealing the bore of the bone. A largest outer diameter of collar 14, which is at body 46, is greater than the second diameter of counter bore 34 at the entry point of the bone. Also, a smallest outer diameter of body 46 is greater than the second diameter, which keeps body 46 out of counter bore 34 during insertion of implant 10. Once implant 10 is seated in this position, another component of the implant can be attached to mount 40.

This solves a problem of the prior art in that it utilizes the strong tapered connection of stem 12 within the intramedullary canal while also providing collar 14 for strength and stability. Extension 38 fits within the counter bore 34 in order to facilitate quick and complete sealing of the bore to minimize the risk of infection. Body 46 of collar 14 is also located a short distance from the resected bone surface, ensuring that it will not contact the bone surface to loosen the tapered connection of stem 12.

Figure 8:
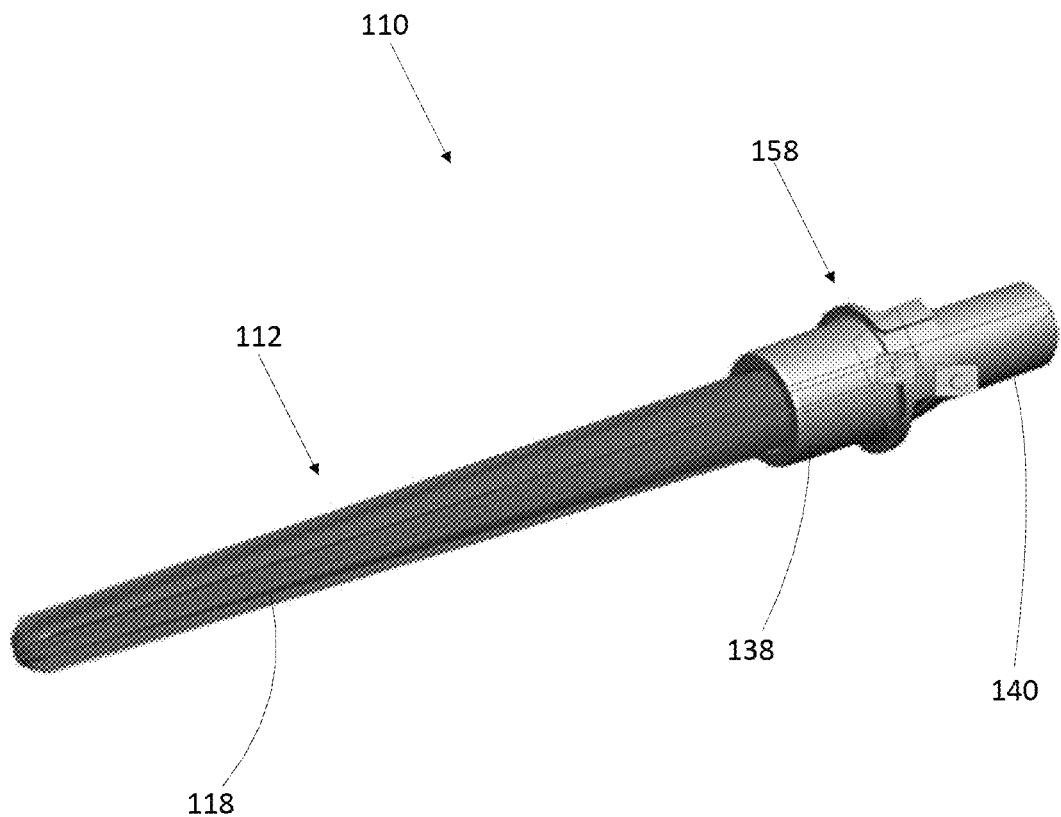
FIG. 8 is a perspective view of a press fit stem with a monolithic collar and connector in accordance with one embodiment of the present invention.

As disclosed previously, press fit stem 10 is comprised of at least three components, including stem 12, collar 14, and connector 16. In an alternative embodiment, a press fit stem 110 includes only two components as a stem 112 and an adapter 158, as shown in FIG. 8. Adapter 158 is a monolithic component that is essentially made of collar 14 and connector 16 in a single unit. Adapter 158 therefore includes a mount 140 on the proximal end and extension 138 on the distal end. Other aspects of implant 110 are similar to those of implant 10, with a distinction of the assembly method being that adapter 158 is taper fit onto a proximal portion of stem 112 to secure the two components together. In an alternative embodiment, adapter 158 can be attached to stem 112 after the insertion of stem 112 into long bone 32.

Figure 9:
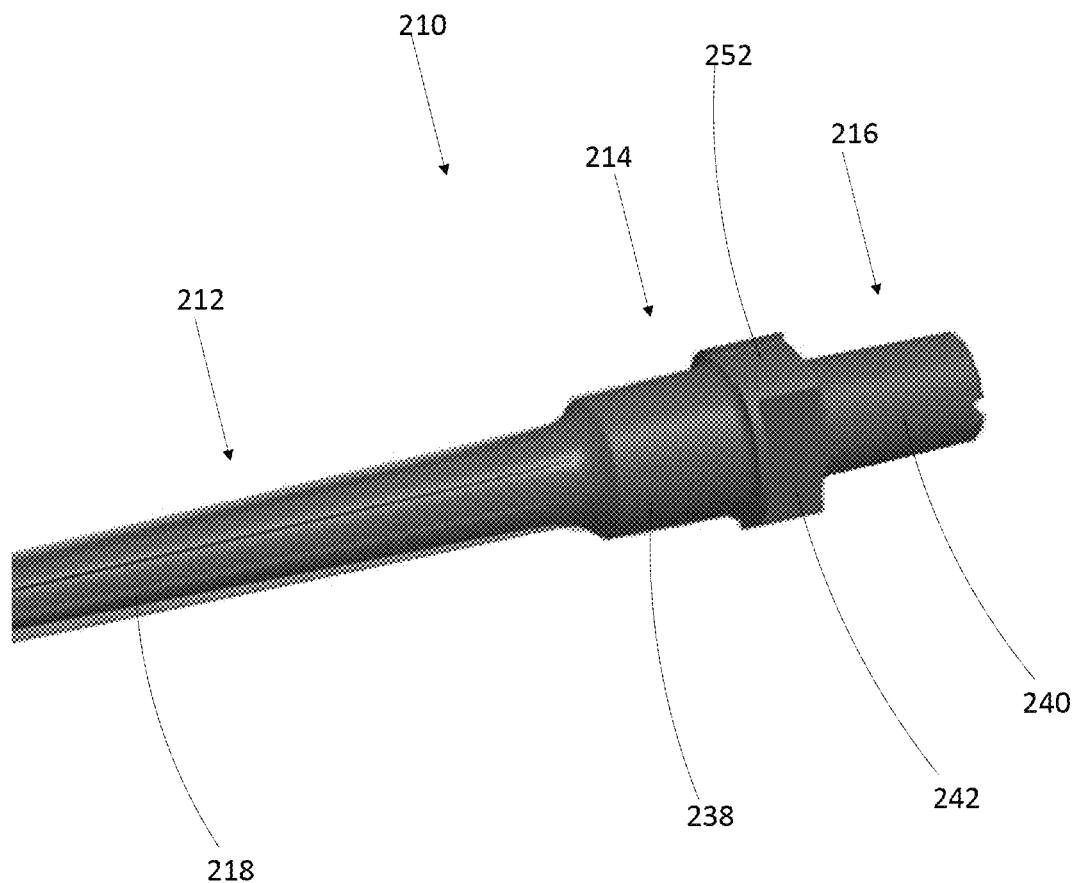
FIG. 9 is a perspective view of a monolithic press fit stem in accordance with one embodiment of the present invention.

FIG. 9 shows an embodiment of a completely monolithic body of press-fit stem 210. As seen in FIG. 9, the monolithic body includes a connector portion 216, including mount 240 and central portion 242, a collar portion 214, including extension 238, and a stem portion 212, including tapered portion 218. Central portion 242 also has resected portions to give it a noncircular cross section for mating with an engagement tool. In the embodiment shown in FIG. 9, extension 238 has a constant diameter such that it is considered cylindrical. Implant 210 is similar in nature a monolithically constructed version of implant 10. The external contours of implant 210 can be identical to those of implant 10 so that it functions identically when implanted according to the method described above. The monolithic press fit stem 210 is inserted into long bone 32 in substantially the same manner as press fit stem 10 and 110. The monolithic body may also be comprised of, in part or in whole, titanium or cobalt chromium, or other surgical grade materials. Stem 210 can be made by 3D printing or additive manufacturing so that it can include both porous and non-porous portions while remaining a monolithic body.

Figure 10:
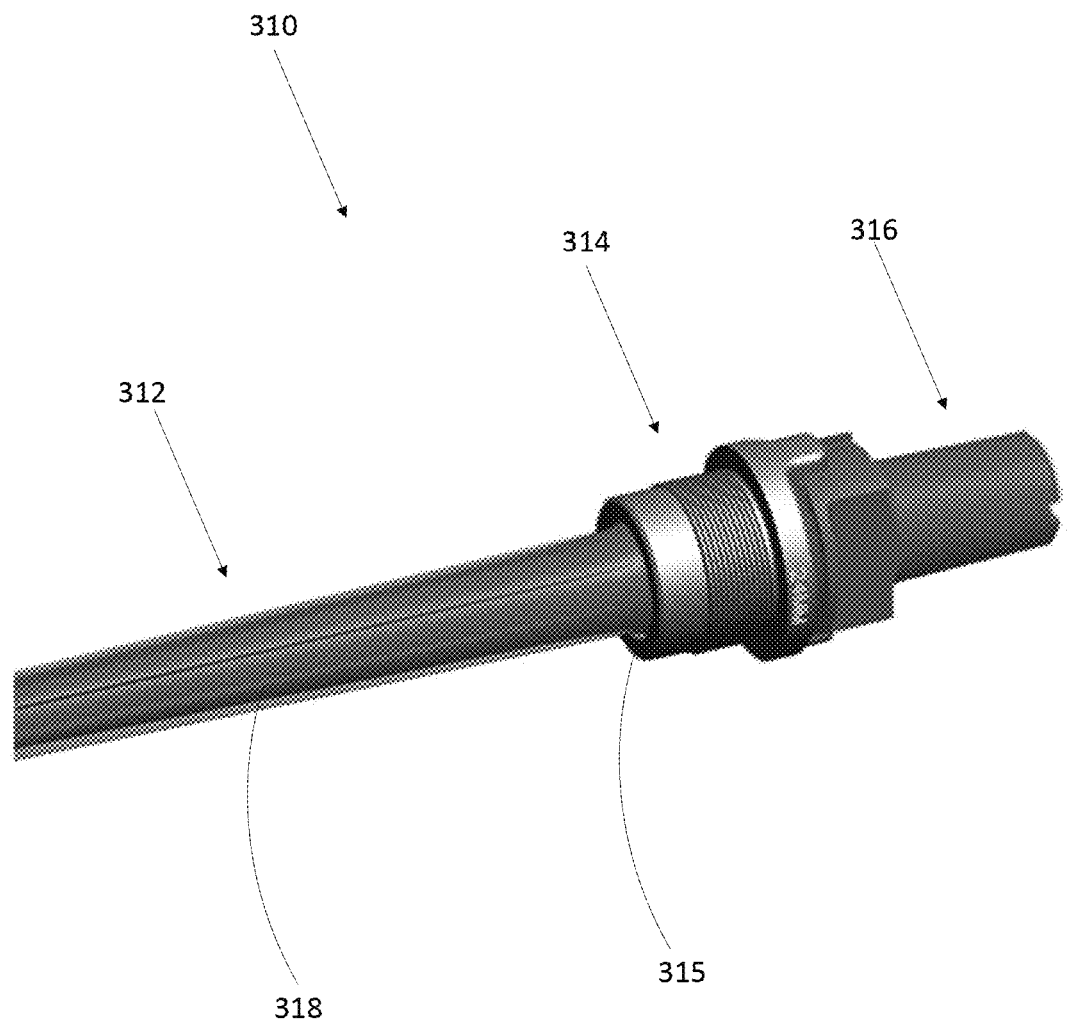
FIG. 10 is a perspective view of a press fit stem with part of a modifiable adapter in accordance with one embodiment of the present invention.
Figure 11:
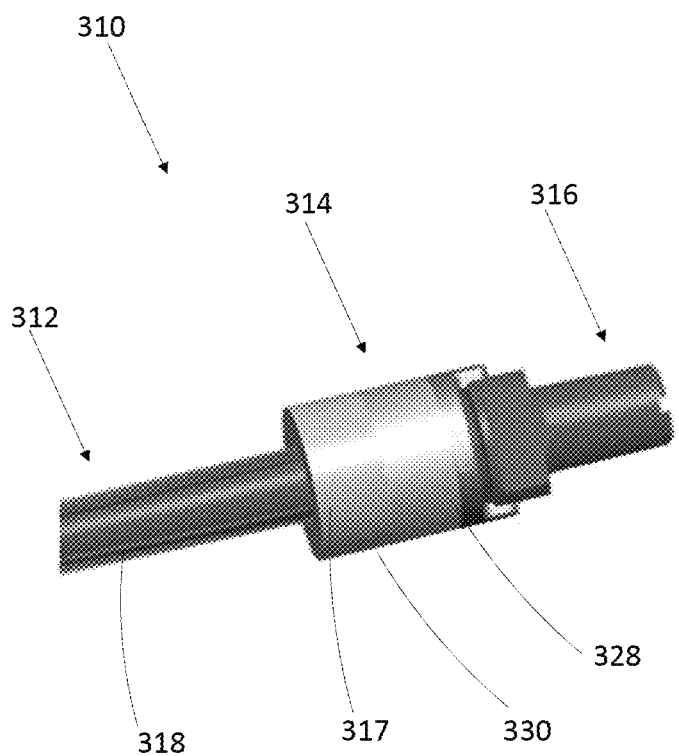
FIG. 11 is a perspective view of the press fit stem shown in FIG. 10 with a porous collar in accordance with one embodiment of the present invention.
Figure 12:
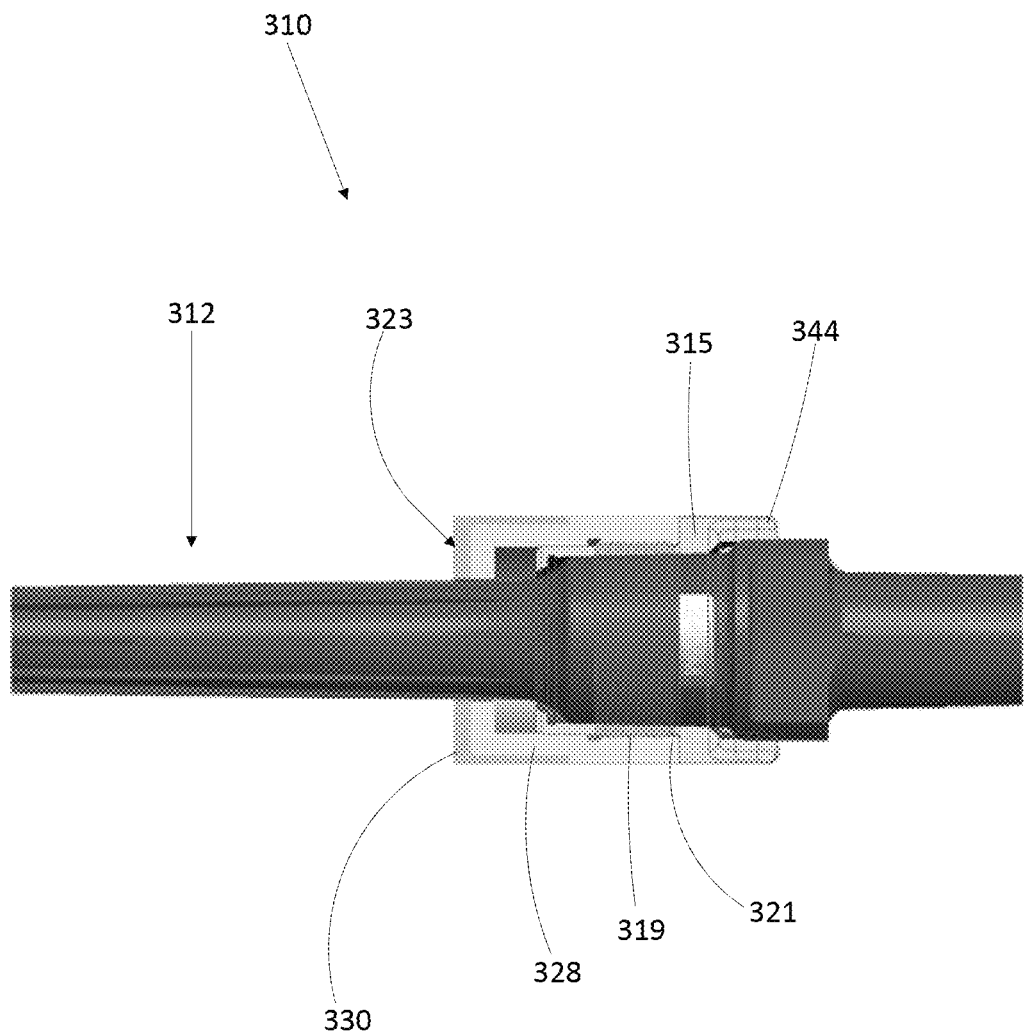
FIG. 12 is a partial cross-sectional view of the press fit stem assembly of FIG. 11.

FIGS. 10-12 show another embodiment in accordance with the present invention in which a press fit stem 310 includes an adjustable collar 214. Collar 214 includes an inner hollow body portion 315 adjustably connected to an outer hollow body portion 317. Aside from collar 314, stem 312 and connector 316 are similar to those of implant 10, and collar 314 taper locks with connector 316 such that it interacts with stem 312 and connector 316 in a similar fashion as well. In fact, implant 10 can be used after substituting collar 314 for collar 14. Adapter 258 has a threaded portion 254.

Collar 314 has a constant outer diameter such that is cylindrical. Collar 314 is bored along its longitudinal axis such that it can slide over stem 312 and be received by connector 316. An outer surface of inner hollow body portion 315 includes a threaded section 319 to mate with a threaded section 321 on an inner surface of outer hollow body portion 317. This allows collar 314 to be adjusted once stem 312 is inserted into tapered bore 36 of long bone 32.

Collar 314, shown in FIG. 11, has a solid, non-porous portion 328 and a porous portion 330, the latter forming at least a portion of an outer surface of outer hollow body portion 317. Porous portion 330 is meant to be positioned adjacent to the long bone 32 within counter bore 34 to promote bone ingrowth into the porous portion 330. The bone ingrowth will cause press fit stem 310 to integrate with long bone 32 for long-term stabilization. Bone ingrowth will also cause press fit stem 310 to become an integral construct leading to a sturdier implant. As such, the patient will experience more success with the implant and less need for future revisions. Alternatively, as discussed below, counter bore 34 can be omitted entirely and collar 314 can remain proximal to the planar resected bone surface and outside of tapered bore 36, while still allowing for bone growth between the distal end of collar 314 and the planar resected bone surface.

Outer hollow body portion 317 has a distal end that defines an aperture 323 through which stem 312 extends when the two are connected. A diameter of the aperture 323 is substantially the same as an outer diameter of stem 312. Of course, as stem 312 is tapered, aperture 323 must accommodate the largest diameter at the proximal end of stem 312.

Implantation of press fit stem 310 involves first assembling its components, with outer hollow body portion 317 threaded or screwed proximally on inner hollow body portion 315 to shorten the length of collar 314 to or near its shortest possible length. Once implant 310 is inserted, to ensure that collar 314 is seated properly within counter bore 34, outer hollow body portion 317 is rotated around inner hollow body portion 315 to lengthen collar 314 and to decrease the distance between the distal surface of collar 314 and the distal surface of counter bore 34. That is, while extension 38 of implant 10 is seated to a particular depth of counter bore 34 as dictated by the taper fit of stem 12 within counter bore 34 and by the overall fit of the components of implant 10, implant 310 can be adjusted after implantation so that outer hollow body portion 317 is extended into counter bore 34 to provide a maximum amount of area between its outer surface and the bone surface to allow for bone ingrowth. The distal end of collar 314 remains separated from the bottom, proximally facing surface of counter bore 34 to maintain the secure seating of implant 310, as described above.

The initial insertion of implant 310 may or may not result in collar 314 being disposed within counter bore 34. The outer surface of outer hollow body portion 317 can be provided with markings to show its depth within counter bore 34 to avoid contacting outer hollow body portion 317 to the distal surface of counter bore 34. Alternatively, outer hollow body portion 317 can be extended to the distal surface of counter bore 34 and then gently moved proximally a short distance to ensure a gap between the proximally facing bone surface and outer hollow body portion 317. In either case, outer hollow body portion 317 is intended to be finally implanted to a depth less than the depth of counter bore 34.

The threaded connection of collar 314 is toleranced to provide a strong friction fit between outer and inner hollow body portions 317, 315 so that once a final configuration of collar 314 is set, the two body portions 317, 315 will not move or rotate with respect to one another based on the normal stresses and forces on implant 310 during movement of the patient.

In an alternative embodiment, implant 310 is inserted without a counter bore 34 in long bone 32. This embodiment may be used when there is not enough long bone 32, or the long bone 32 is not healthy enough, to allow for a counter bore 34. In such instances, only a tapered bore 36 is reamed into long bone 32. The distal end of implant 310 is inserted into the tapered bore 32 to form a press-fit, or taper lock, between the tapered portion 318 of stem 312 and long bone 32. Outer hollow body portion 317 is then rotated around inner hollow body portion 315 to lengthen collar 314. This allows for implant 310 to be adjusted after implantation so that outer hollow body portion 317 is extended toward the resected plane of long bone 32 to provide the proper distance between the distal surface of outer hollow body portion 316 and the bone surface to allow for bone ingrowth.

A method of making any of the implant disclosed herein can include first producing a stem made of a non-porous material. A collar is additively manufactured to include both its porous and non-porous portions as a solid construct. In other embodiments, the stem and any other components of the implant, such as the connector can be additively manufactured.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of implanting a medical implant comprising the steps of:
   reaming a tapered bore through an end surface of a long bone and into an intramedullary canal of the long bone to a first depth, the tapered bore having a first diameter at an entry point at the surface of the bone;
   reaming a counter bore through the end surface to form a proximally-facing surface at a bottom of the counter bore inside the long bone at a second depth disposed between the end surface and the first depth, the counter bore having a third diameter that is greater than the first diameter; and
   fully seating a tapered portion of a stem of a medical implant into the tapered bore so as to form a press-fit between the tapered portion of the stem and the long bone, the medical implant further comprising a collar disposed about at least a portion of the stem, the collar having a first end and a second end, the first end having a second diameter greater than the first diameter and less than the third diameter and having an end surface defining a first extent of the collar, and
   wherein, once the tapered portion of the stem is fully seated within the tapered bore, a gap is formed within the counter bore between the end surface of the collar and the proximally-facing surface of the counter bore.

2. The method of claim 1, further comprising rotating an outer hollow body portion of the collar about an inner hollow body portion so that mating threaded sections of the outer and inner hollow body portions facilitate advancement of the outer hollow body portion toward the proximally-facing surface of the counter bore.

3. The method of claim 2, wherein the outer hollow body portion includes a porous structure.

4. The method of claim 1, wherein the end surface of the collar is a planar surface, and the collar has a constant outer diameter along its length.

5. The method of claim 1, wherein the step of fully seating the tapered portion of the stem into the tapered bore includes maintaining the collar outside of intramedullary canal.

6. The method of claim 1, further comprising connecting the collar to the stem so that the tapered portion extends from the first end of the collar and a connector of the stem extends from the second end of the collar.

7. The method of claim 6, wherein the connecting step includes forming a taper lock between the stem and the collar.

8. The method of claim 6, wherein the connecting step further includes sliding the collar over the tapered portion of the stem until the second end of the collar is positioned adjacent to a central portion of the stem, the central portion having a cross-sectional dimension greater than a maximum cross-sectional dimension of the tapered portion of the stem.

9. The method of claim 8, wherein the connecting step further includes positioning tabs projecting from the second end of the collar within notches formed in the central portion of the stem.

10. The method of claim 1, wherein the long bone is a femur.

11. The method of claim 1, further comprising a step of attaching another component of the implant to the stem.

12. The method of claim 1, further comprising a step of resecting the long bone at a location along a diaphysis of the bone so as to remove a metaphysis, an epiphysis, and a portion of the diaphysis and so as to form the end surface of the long bone.

13. The method of claim 12, wherein the reaming steps are performed through the end surface of the long bone.

14. The method of claim 1, wherein a portion of the collar faces a sidewall of the counter bore to facilitate bone ingrowth.

15. A method of implanting a medical implant comprising the steps of:
resecting a long bone along a diaphysis thereof so as to form a resected surface and to remove a metaphysis, an epiphysis, and a portion of the diaphysis of the long bone;
reaming a tapered bore through the resected surface of the long bone and into an intramedullary canal thereof;
reaming a counter bore through the resected surface of the long bone to form a proximally-facing surface at a bottom of the counter bore, wherein the counter bore is coaxial to the tapered bore; and
fully seating a tapered portion of a stem of a medical implant into the tapered bore so as to form a press-fit between the tapered portion of the stem and the long bone and so that a collar disposed at an end of the stem is offset from the proximally-facing surface so as to form a gap within the counter bore between the proximally-facing surface and the collar.

16. The method of claim 15, further comprising adjusting the collar so that at least a portion thereof is moved relative to the stem, wherein the adjusting step is performed after the fully seating step.

17. The method of claim 16, wherein the adjusting step includes rotating an outer portion of the collar relative to an inner body portion of the collar.

18. The method of claim 15, further comprising connecting the collar to the stem such the tapered portion extends from a first end of the collar and a connector of the stem extends from a second end of the collar.

19. The method of claim 18, further comprising a step of attaching another component of the implant to the connector of the stem.

20. The method of claim 15, wherein the collar includes a porous portion, and the fully seating step includes positioning the porous portion adjacent the resected surface of the long bone.

21. The method of claim 15, wherein the long bone is a femur.

* * * * *